United States Patent [19]

Costantini et al.

[11] Patent Number: 5,331,103

[45] Date of Patent: Jul. 19, 1994

[54] PROCESS FOR MONOHYDROXYLATION OF PHENOLIC COMPOUNDS

[75] Inventors: Michel Costantini; Dominique Laucher, both of Lyons, France

[73] Assignee: Rhone-Poulenc Chimie, Courbevoie, France

[21] Appl. No.: 22,896

[22] Filed: Feb. 26, 1993

[30] Foreign Application Priority Data

Feb. 26, 1992 [FR] France ................... 92 02210
Feb. 26, 1992 [FR] France ................... 92 02211

[51] Int. Cl.$^5$ .............................................. C07C 37/60
[52] U.S. Cl. .................................. 568/803; 568/717; 568/741; 568/771; 568/798
[58] Field of Search ............... 568/741, 763, 803, 771, 568/798

[56] References Cited

U.S. PATENT DOCUMENTS

| | | | |
|---|---|---|---|
| 4,078,006 | 3/1978 | Umemura et al. | 568/771 |
| 4,214,105 | 7/1980 | Seifert et al. | 568/771 |
| 5,097,078 | 3/1992 | Constantini et al. | 568/771 |

FOREIGN PATENT DOCUMENTS

| | | | |
|---|---|---|---|
| 0480800A1 | 4/1992 | European Pat. Off. | |
| 2064497 | 7/1971 | Fed. Rep. of Germany | 568/803 |
| 2071464 | 9/1971 | France | |
| 2266683 | 10/1975 | France | |

OTHER PUBLICATIONS

Chemical Abstracts, vol. 113, No. 3, Jul. 16, 1990, Columbus, Ohio; abstract no. 23364n, K. Yorozu et al, "Preparation of polyhydric phenols as stabilizers & antioxidants", p. 606, col. 2, & JP-A-0 278 641 (Mitsui Petrochemical Industries, Ltd.)

*Primary Examiner*—Werren B. Lone
*Attorney, Agent, or Firm*—Burns, Doane, Swecker & Mathis

[57] ABSTRACT

The present invention relates to a process for monohydroxylation of phenolic compounds which allows an increase in the amount of para isomer.

The invention relates to a process for monohydroxylation of a phenolic compound having a hydrogen atom in the para position to the hydroxyl group, for the purpose of obtaining a dihydroxylated aromatic compound by reacting the initial phenolic compound with hydrogen peroxide in the presence of an effective amount of a strong acid and of a ketonic compound, said process being characterized by the fact that the reaction is carried out in the presence of an effective amount of a polar aprotic organic solvent with a basicity such that it has a "donor number" below 25.

38 Claims, No Drawings

PROCESS FOR MONOHYDROXYLATION OF PHENOLIC COMPOUNDS

BACKGROUND OF THE INVENTION

The present invention relates to a process for monohydroxylation of phenolic compounds for the purpose of obtaining dihydroxylated aromatic compounds. The invention relates, more particularly, to a process for monohydroxylation of phenols and phenol ethers using hydrogen peroxide.

Several processes for hydroxylation of phenols are described in the prior art.

For example, the patent FR-A 2 071 464 which relates to a very important industrial process for hydroxylation of phenols and phenol ethers.

This process involves hydroxylation using oxygenated water in the presence of a strong acid. The most widely used of these strong acids are sulphuric acid, paratoluene-sulphonic acid and perchloric acid.

Hydroxylation of phenol, carried out under the conditions described, results in a mixture of hydroquinone and pyrocatechol with a predominance of this latter since the hydroquinone/pyrocatechol ratio most frequently varies between 0.3 and 0.7.

A proposal has been made in FR-A 2 266 683 to perfect this process which involves hydroxylation being carried out in the presence of a ketone. There is an improvement in the yield of hydroquinone and pyrocatechol from the reaction. However, all the examples described give a greater quantity of pyrocatechol than of hydroquinone.

The known processes thus mainly yield pyrocatechol.

It transpires that in order to comply with the fluctuating market demand, it is important to have an industrial process which allows an increase in the production of hydroquinone formed in relation to the amount of pyrocatechol.

In order to provide a solution to this technical problem, FR-A 2 667 598 discloses a process which permits an increase in the amount of hydroquinone formed in relation to the amount of pyrocatechol, and which in its preferred variant allows more hydroquinone to be obtained than pyrocatechol.

This process consists in carrying out hydroxylation of the phenol in the presence of an effective amount of a strong acid, said process being characterised by the fact that the reaction is carried out in the presence of a ketonic compound selected from benzophenone and benzophenones, the hydrogen atoms of the aromatic ring of which can be substituted by an electron-donor group.

In accordance with the process described in FR-A 2 667 598, the presence of the ketonic compound such as selected during hydroxylation of the phenol affects the positional selectivity of the reaction, and hydroquinone/pyrocatechol ratios varying between 1.0 and 1.13 are advantageously obtained.

Continuing the research, the inventors have perfected the invention described in FR-A 2 667 598 and found that even higher hydroquinone/pyrocatechol ratios could be obtained by adding to the reaction mixture a small amount of an organic aprotic solvent with certain polarity and basicity properties.

SUMMARY OF THE INVENTION

To be more precise, the present invention relates to a process for monohydroxylation of a phenolic compound having a hydrogen atom in the para position to the hydroxyl group, for the purpose of obtaining a dihydroxylated aromatic compound by reacting the initial phenolic compound with hydrogen peroxide in the presence of an effective amount of a strong acid and a ketonic compound, said process being characterised in that the reaction is carried out in the presence of an effective amount of a polar aprotic organic solvent with a basicity such that it has a "donor number" less than 25.

A first variant of the process of the invention involves the use of a polar organic solvent of low basicity, that is to say one which has a polarity such that its dielectric constant is greater than or equal to 20 and a basicity such that it has a "donor number" of less than 25.

A second variant of the process of the invention consists in using an organic solvent which is less polar but basic, that is to say one which has a polarity such that its dielectric constant is less than about 20 and which has a basicity such that it has a "donor number" which is above or equal to 15 and less than 25.

The invention is preferably used in the hydroxylation of phenol into hydroquinone and pyrocatechol.

DETAILED DESCRIPTION OF THE PREFERRED EMBODIMENTS OF THE INVENTION

It has now been discovered that the presence of a solvent with properties such as those defined hereinabove can increase the hydroquinone/pyrocetachol ratio.

Thus, in accordance with the present invention, ratios in the order of 1.1 to 1.3 or above can be obtained, depending on the type of organic solvent used.

It should be noted that the selection of organic solvent to be used is quite critical and that it is important to use an aprotic organic solvent which is very polar but not very basic or which is not very polar but basic.

Thus, if an aprotic organic solvent is used of great polarity and great basicity such as dimethylformamide or N-methylpyrrolidone, the sought effect is not obtained.

Moreover, it has been surprisingly noted that the effect of the solvent selected in accordance with the invention was given irrespective of the type of ketonic compound.

Thus, it becomes possible, by using the process according to the invention, to very easily adapt the amount of hydroquinone to market needs, simply by adding sufficient organic solvent.

The selection of organic solvent is subject to several requirements.

A first feature of the organic solvent is that it is aprotic and stable in the reaction medium.

The term, "aprotic solvent" is used to refer to a solvent which has no protons to free according to the Lewis theory.

The present invention excludes solvents which are not stable in the reaction medium and which are degraded either by oxidation or by hydrolysis. Examples of reaction solvents which do not conform with the invention may be cited as solvents of the ester type derived from carboxylic acids such as, in particular, methyl or ethyl acetate, methyl or ethyl phthalate, methyl benzoate etc.

Organic solvents which are suitable for use with the process of the invention must satisfy certain requirements in terms of their polarity and basicity characterised by the donor number.

A first class of organic solvents which is perfectly suitable fop use with the process of the invention are organic solvents which are polar and of low basicity.

In accordance with the invention, an organic solvent is selected which has a dielectric constant which is greater than or equal to 20. The upper limit has no critical value. Use is preferably made of an organic solvent which has a high dielectric constant, preferably between 25 and 75.

The organic solvent with the polarity features described hereinabove must also satisfy certain basicity requirements. In fact, said solvent must not be too basic. To determine whether a solvent satisfies this requirement, its basicity is assessed by referring to a "donor number". A polar organic solvent is selected which has a donor number less than 25, preferably less than or equal to 20. The lower limit is not critical. An organic solvent is preferably selected which has a donor number of between 2 and 17.

As lap as the other class of solvents claimed is concerned, the properties of said solvents are defined hereinafter.

The solvents in this category are organic solvents of low polarity but basic.

In accordance with the invention, an organic solvent is selected which has a dielectric constant of less than about 20. The lower limit is not critical. An organic solvent is preferably used which has a low dielectric constant, preferably between 2 and 15.

As far as its basicity is concerned, it must be such that it has a "donor number" which is above or equal to 15 and less than 25. An organic solvent is preferably selected which has a donor number of between 15 and 25.

In order to determine whether the organic solvent satisfies the dielectric constant conditions mentioned hereinabove, reference may be made, amongst others, to the tables in the work: "Techniques of Chemistry. II"-Organic solvents- p. 536 and following, 3rd edition (1970).

Regarding the requirements for basicity of the organic solvent to be used, it will be recalled that the "donor number", abbreviated as DN, gives an indication as to the nucleophilic nature of the solvent and reveals its capacity for giving its doublet.

In the work by Christian REINHARDT, [Solvents and Solvent Effects in Organic Chemistry- VCH p. 19 (1988)], the term, "donor number" is given which is defined as the negative ($-\Delta H$) of the enthalpy (Kcal/mol) of the interaction between the solvent and the antimony pentachloride in a diluted solution of dichlorethane.

Examples of polar aprotic organic solvents satisfying the aforementioned basicity features and which are capable of being used in the process of the invention may be cited, in particular, as:
- nitrated compounds such as nitromethane, nitroethane. 1-nitropropane, 2-nitropropane or mixtures thereof, nitrobenzene,
- alphatic or aromatic nitriles such as acetonitrile, propionitrile, butanenitrile, isobutanenitrile, benzonitrile, benzyl cyanide,
- tetramethylene sulphone (sulpholane),
- propylene carbonate.

It is also possible to use a mixture of solvents.

Of the afore-mentioned solvents, acetonitrile is preferably used.

As far as the other class of solvents claimed is concerned, examples will be given hereinafter of aprotic solvents of low polarity and basicity which can be used in the process of the invention:
- aliphatic, cycloaliphatic or aromatic ether-oxides, and more particularly, diethyl oxide, dipropyl oxide, diisopropyl oxide, dibutyl oxide, t-butyl methyl ether, dipentyl oxide, diisopentyl oxide, ethylene glycol dimethylether (or 1,2-dimethoxy ethane), diethylene glycol dimethyl ether (or 1,5-dimethoxy 3-oxapentane), dioxane, tetrahydrofuran,
- neutral phosphoric esters such as, in particular, trimethyl phosphate, triethyl phosphate, butyl phosphate, triiso butyl phosphate, tripentyl phosphate, ethylene carbonate.

It is also possible to use a mixture of solvents.

In accordance with the process of the invention a dihydroxylated aromatic compound is prepared by hydroxylation of a phenolic compound using hydrogen peroxide.

In the description of the present invention which is given hereinafter, the term, "aromatic compound" is used to refer to the conventional notion of aromaticity such as defined in writings, in particular in the work by Jerry MARCH, Advanced Organic Chemistry, 3rd edition, John Wiley and Sons, 1985, p. 37 and following.

The present invention relates more particularly to the phenolic compound of the general formula (I):

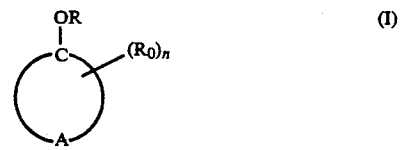

wherein:
- A symbolises a residue of a monocyclic, bicyclic or polycyclic aromatic carbocyclic radical or a divalent radical constituted of a chain of two or more monocyclic aromatic carbocyclic radicals,
- R represents a hydrogen atom or a hydrocarbon radical with 1 to 24 carbon atoms which can be a saturated or unsaturated, linear or branched aliphatic radical or a saturated or unsaturated, monocyclic or polycyclic cycloaliphatic radical,
- $R_o$ represents one or more substituents, identical or different,
- n is a number less than or equal to 4.

The process according to the invention is used with any phenolic compound corresponding to general formula (I), and, more particularly, with any phenolic compounds of formula (I), wherein:
- the radical R represents one of the following groups:
  - a hydrogen atom
  - a linear or branched alkyl radical with 1 to 6 carbon atoms,
  - a cyclohexyl radical,
  - a phenyl radical,
  - a benzyl radical,
- the $R_o$ radical(s) represents/represent one of the following groups:
  - a hydrogen atom,
  - a linear or branched alkyl radical with 1 to 6 carbon atoms,
  - a linear or branched alkenyl radical with 2 to 6 carbon atoms, an alkoxy radical of the $R_1$-o- type where $R_1$ represents a linear or branched alkyl radical with 1 to 6 carbon atoms, an alkyl group with 2 to 6 carbon atoms, a —$COOR_2$ group where $R_2$ represents a linear or branched alkyl radical with 1 to 4 carbon atoms, a halogen atom, preferably fluorine, chlorine, bromine, a —$CF_3$ group.

n is a number equal to 0, 1, 2 or 3.

The phenolic compound of formula (I) can be the carrier of one or more constituents. Examples of constituents are given hereinabove, but the list is in no way limitative. Any substituent can be present in the cycle as long as it does not interfere with the desired product.

Of the compounds of formula (I), use is made most particularly of those whose residue (A) represents:

a monocyclic or polycyclic aromatic carbocyclic radical with cycles capable of forming amongst themselves an orthocondensed system corresponding to formula (Ia):

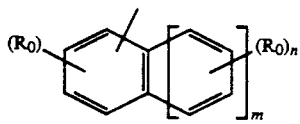

in which formula (Ia), m represents a number equal to 0, 1 or 2 and the symbols $R_o$ and n which may be identical or different have the meaning given hereinabove, a radical constituted of a chain of two or more monocyclic aromatic carbocyclic radicals corresponding to formula (Ib):

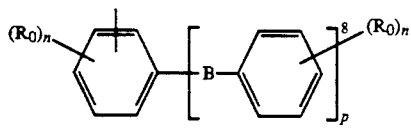

in which formula (Ib), the symbols $R_o$ and n which may be identical or different have the meaning given hereinabove, p is a number equal to 0, 1, 2 or 3 and B represents:

a valency linkage an alkylene or alkylidene radical with 1 to 4 carbon atoms. preferably a methylene or isopropylidene radical, one of the following groups:

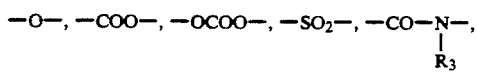

in these formulae, $R_3$ represents a hydrogen atom or an alkyl radical with 1 to 4 carbon atoms, a cyclohexyl or phenyl radical.

The compounds of formula (I) used preferably correspond to formulae (Ia) and ( Ib ) wherein:

$R_o$ represents a hydrogen atom, a linear or branched alkyl or alkoxy radical with 1 to 6 carbon atoms, preferably 1 to 4 carbon atoms, a cyclohexyl radical, a phenyl radical, B symbolises a valency linkage, an alkylene or alkylidene radical with 1 to 4 carbon atoms or an oxygen atom.

m is equal to 0 or 1, n is equal to 0,1 or 2, p is equal to 0 or 1.

The invention is concerned, more particularly, with phenolic compounds of general formula (I'):

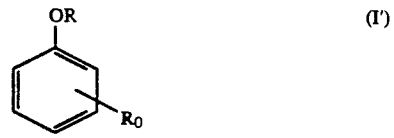

wherein R and $R_o$ which may be identical or different represent a hydrogen atom, an alkyl radical with 1 to 4 carbon atoms, a cyclohexyl radical, a phenyl radical.

Still more preferably, compounds of formula (I') are selected wherein R represents a hydrogen atom and $R_o$ represents a hydrogen atom, a methyl radical, a methoxy radical.

Examples of phenolic compounds of formula (I) capable of being used in the process of the invention can be given, in particular, as:

those in which the residue A corresponds to formula (Ia) wherein m and n are equal to 0, such as phenol or anisol.

those in which the residue A corresponds to formula (Ia) wherein m is equal to 0 or n is equal to 1, such as orthocresol, metacresol, 2-methoxyphenol, 2-ethylphenol, 3-ethylphenol, 2-propylphenol, 2-sec-butyl phenol, 2-tert-butyl phenol, 3-tert-butyl-phenol, 2-methoxy phenol, 3-methoxy phenol, methyl salicylate, 2-chloro phenol, 3 -chloro phenol, those in which the residue A corresponds to formula (Ia) wherein m is equal to 0 and n is equal to 2, such as 2,3-dimethyl phenol, 2,5-dimethyl phenol, 2,6-dimethyl phenol, 3,5-dimethyl phenol, 2,3-dichloro phenol, 2,5-dichloro phenol, 2,6-dichloro phenol, 3,5-dichloro phenol, those in which the residue A corresponds to the formula (Ia) wherein m is equal to 0 and n is equal to 3, such as 2,3,5-trimethyl phenol, 2,3,6-trimethyl phenol, 2,6-di-tert butyl phenol, 3,5-di-tert butyl phenol, 2,3,5-trichloro phenol, 2,3,6-trichloro phenol, those wherein the residue A corresponds to Formula (Ia) wherein m is equal to 1 and n is equal to 1, such as 1-hydroxy naphthalene, those wherein the residue A corresponds to the formula (Ib) wherein n is greater than or equal to 1, such as 2-phenoxy phenol, 3-phenoxy phenol.

The present process is most particularly suitable for the preparation of hydroquinone and pyrocatechol from phenol.

In accordance with the process of the invention, a polar aprotic organic solvent is used during the process for monohydroxylation of the phenolic compound of formula (I) , carried out in the presence of a strong acid and of a ketonic compound.

Since the effect of the solvent is ascertained irrespective of the kind of ketonic compound used, it is possible to use any ketonic compound, and more particularly those corresponding to formula (II):

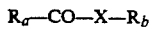

in which formula (II):

$R_a$ and $R_b$ which may be identical or different represent hydrocarbon radicals with 1 to 30 carbon atoms or which together form a divalent radical, possibly substituted by one or more halogen atoms or functional groups which are stable under the conditions of the reaction, X represents a valency linkage, a —CO— group, a —CHOH group or a —(R)$_n$— group, R representing an alkylene group with preferably 1 to 4 carbon atoms, and n is a whole number selected between 1 and 16.

In the formula (II), $R_a$ and $R_b$ represent more particularly:

linear or branched alkyl radicals,
linear or branched alkenyl radicals,
cycloalkyl or cycloalkenyl radicals comprising 4 to 6 carbon atoms,
mono- or polycyclic aryl radicals, in the latter case the cycles forming amongst themselves an ortho- or ortho and pericondensed system or being linked together by a valency linkage,
arylalkyl or arylakenyl radicals,
$R_a$ and $R_b$ can form together an alkylene or alkenylene radical with 3 to 5 carbon atoms, possibly substituted by an alkyl radical of low carbon content or by a cycloalkyl or cycloalkenyl radical with 4 to 6 carbon atoms; 2 to 4 of the carbon atoms of the alkylene or alkenylene radicals being capable of forming part of one or two benzene cycles which may be substituted by 1 to 4 hydroxyl groups and/or alkyl groups and/or alkoxy with a low carbon content.

In the following exposition of the invention, the terms, "alkyl group of low carbon content" is used to refer to a linear or cross-linked alkyl group which usually has 1 to 4 carbon atoms.

The afore-mentioned hydrocarbon radicals can be substituted by 1 or more, preferably by 1 to 4, alkyl groups of low carbon content or functional groups such as hydroxyl groups, low carbon content alkoxy groups, hydroxycarbonyl groups, alkoxy-carbonyl groups with 1 to 4 carbon atoms in the alkyl group, a nitrile group, —SO$_3$H, nitro or by one or more halogen atoms, in particular chlorine or bromine.

Preferably, $R_a$ and $R_b$ represent more particularly:
linear or branched alkyl radicals with 1 to 10 carbon atoms,
linear or branched alkenyl radicals with 2 to 10 carbon atoms,
cycloalkyl or cycloalkenyl radicals with 4 to 6 carbon atoms.
phenyl radicals which may be substituted by 1 to 4 alkyl and/or hydroxyl and/or alkoxy groups,
phenylalkyl or phenylakenyl radicals comprising 1 (or 2) to 10 carbon atoms in the aliphatic part, and more particularly 1 (or 2) to 5 carbon atoms in the aliphatic part,
$R_a$ and $R_b$ can form together an alkenyl or alkenylene radical with 3 to 5 carbon atoms, possibly substituted by 1 to 4 alkyl radicals of low carbon content.

Specific examples of ketones which can be used in the process of the invention can be cited, more particularly, as:

acetone,
2-butanone
methylisopropylketone
pivalone
2-pentanone
3-pentanone
4-methyl-2-pentanone
3,3-dimethyl-2-butanone
2-hexanone
3-hexanone
2-hexanone
4-heptanone
2-octanone
3-octanone
2-nonanone
5-nonanone
8-pentadecanone
2-methyl-3-hexanone
5-methyl-2-hexanone
5-methyl-3-hexanone
2,4-dimethyl-3-pentanone
5-methyl-3-heptanone
methylvinylketone
mesityl oxide
1-penten-3-one
3-penten-2-one
5-hexen-2-one
5-methyl-3-hexen-2-one
6-methyl-5-hepten-2-one
diacetyl
diacetone-alcohol
acetoin
2,3-butanedione
2,4-pentanedione
2,5-hexanedione
dicyclohexylketone
methylcyclohexylketone
acetophenone
n-propiophenone
n-butyrophenone
isobutyrophenone
n-valerophenone
2-methyl-acetophenone
2,4-dimethyl-acetophenone
phenylvinylketone
benzophenone
2-methyl-benzophenone
2,4-dimethyl-benzophenone
4,4'-dimethyl-benzophenone
2,2'-dimethyl-benzophenone
4,4'-dimethoxy-benzophenone
4-hydroxy-benzophenone
4,4'-dihydroxy-benzophenone
4-benzoyl-biphenyl
benzoin
4,4'-dihydroxy-benzoin
2,4-dimethyl-benzoin
4,4'-dimethyl-benzoin
4,4'-dimethoxy-benzoin
4,4'-difluoro-benzoin
α-methoxy-benzoin
α-ethoxy-benzoin
deoxybenzoin
4-hydroxy-deoxybenzoin
4-methyl-deoxybenzoin
4-methoxy-deoxybenzoin
4,4'-dimethoxy-deoxybenzoin
4,4'-difluoro-deoxybenzoin
β-phenylpropiophenone
dibenzylketone
δ-phenylvalerophenone
1,1-diphenyl-2-propanone
1,3-diphenylpropanone benzalacetone
benzalacetophenone
benzil
cyclopentanone
2-methyl-cyclopentanone
cyclohexanone
2-methyl-cyclohexanone
3,3,5,5-tetramethyl-cyclohexanone
2-cyclopentenone
2-cyclohexenone
α-isophorone
β-isophorone
cyclohexenyl-cyclohexanone
α-indanone
βindanone
αtetralone
fluorenone Of all the afore-mentioned ketones, use is preferably made of the ketonic compounds which themselves have a para-orienting effect such as disclosed in FR-A 2 667 598.

Thus, use is made most particularly of ketonic compounds corresponding to the general formula (IIa):

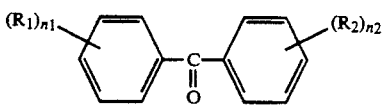

(IIa)

in which formula (IIa):
R₁ and R₂ which may be identical or different represent a hydrogen atom or an electron donor group,
n₁, n₂ which may be identical or different is a number equal to 0, 1, 2 or 3,
possibly, the two carbon atoms in position α in relation to the two carbon atoms bearing the —CO group can be linked together by a valency linkage or by a —CH₂— group thus forming a ketonic cycle which can be saturated but also unsaturated.

As mentioned hereinabove, said ketonic compounds are the objects of the Patent Application FR-A 2 667 598 to which reference has been made in this application.

The term, "electron-donor group" is used to refer to a group such as defined by H. C. BROWN in the work by Jerry MARCH-Advanced Organic Chemistry, chapter 9, pages 243 and 244 (1985).

The electron donor group is selected in such a way that it does not react under the acidity conditions of the invention.

Examples of electron donor groups which are well suited to the invention described in FR-A 2 667 598 are as follows:
linear or cross-linked alkyl radicals with 1 to 4 carbon atoms,
the phenyl radical,
the R₃—O— alkoxy radicals wherein R₃ represents a linear or cross-linked alkyl radical with 1 to 4 carbon atoms or the phenyl radical,
the hydroxyl group,
the fluorine atom.

Examples of ketonic compounds which are particularly suited to the invention described in FR-A 2 667 598 are, in particular, ketonic compounds corresponding to the general formula (II) wherein R₁ and R₂ which may be identical or different represent a hydrogen atom or an electron donor group, preferably in position 4,4′ and n₁ and n₂ which may be identical or different are equal to 0 or 1.

Use is preferably made of ketonic compounds corresponding to formula (II) in which R₁ and R₂ which may be identical or different represent a hydrogen atom; a methyl, ethyl, t-butyl, phenyl radical; a methoxy or ethoxy radical; a hydroxyl group preferably in position 3,3′ or 4,4′.

Specific examples of ketones which can be used in the process of the invention described in FR-A 2 667 598 can be cited, in particular, as:
benzophenone
2-methylbenzophenone
2,4-dimethylbenzophenone
4,4′-dimethylbenzophenone
2,2′-dimethylbenzophenone
4,4′-dimethoxybenzophenone
fluorenone
4-hydroxybenzophenone
4,4′-dihydroxybenzophenone
4-benzoylbiphenyl According to the process of the invention, a polar aprotic organic solvent is used during the process for monohydroxylation of the phenolic compound of formula (I) carried out in the presence of a strong acid and a ketonic compound.

The amount of organic solvent to be used is determined in dependency on the kind of organic solvent selected.

Thus, when a polar organic solvent of low basicity is used, it is determined in such a way that the molar ratio between the number of moles of the organic solvent and the number of moles of the phenolic compound and the number of moles of the phenolic compound of formula (I) varies between 0.1 and 2.0, preferably between 0.25 and 1.0.

If an organic solvent of low polarity and basicity is used, the amount used is determined in such a way that the molar ratio between the number of moles of the organic solvent and the number of moles of the phenolic compound of formula (I) varies between 0.01 and 0.25, preferably between 0.025 and 0.15.

Generally speaking, the amount of solvent to be added is selected as a function of the basicity of the solvent. The amount of solvent used decreases as its basicity increases. In other words, an amount which is towards the lower limit of the range defined hereinabove will be selected when the solvent is of high basicity.

The ketonic compound of formula (II) defined hereinabove is used in an amount defined hereinafter.

Usually, the amount of ketonic compound of formula (II), expressed in moles per mole of hydrogen peroxide, varies between $1.10^{-3}$ mole and 10. It is not necessary to exceed 1.0 mole of ketonic compound per mole of hydrogen peroxide. In practice, the amount of ketonic compound is most often between 0.05 and 1.0 mole per mole of hydrogen peroxide.

The hydrogen peroxide used in accordance with the invention can be in the form of an aqueous solution or an organic solution.

Since aqueous solutions are more easily available commercially, it is preferable if these are used.

Although the concentration of aqueous solution of hydrogen peroxide is not critical per se, it is selected in such a way as to introduce as little water as possible into the reaction medium. Use is generally made of an aqueous solution of hydrogen peroxide with at least 20% by weight $H_2O_2$, and preferably about 70%.

The amount of hydrogen peroxide can go up to 1 mole $H_2O_2$ for 1 mole of phenolic compound of formula (I).

However, in order to obtain a yield which is industrially acceptable it is preferable to use a molar ratio of hydrogen peroxide/phenolic compound of formula (I) of 0.01 to 0.3, and preferably of 0.05 to 0.10.

In order to have a sufficient reaction speed, the initial water content of the medium is restricted to 20% by weight, preferably to 10% by weight.

The contents by weight indicated are expressed in relation to the mixture of phenolic compound of formula (I)/hydrogen peroxide/water.

This initial water corresponds to the water introduced with the reagents, and, in particular, with the hydrogen peroxide.

A strong acid is used in the process of the invention. The term, "strong acid" is used in the present invention to refer to an acid which has a pka in water of less than $-0.1$ and preferably of less than $-1.0$.

The pka is defined as the ionic dissociation constant of the acid/base couple when water is used as the solvent.

Of the acids which comply with this definition, it is preferable to use those which are stable in terms of oxidation by hydrogen peroxide.

It is possible to cite, in particular, halogenated or non-halogenated oxyacids such as sulphuric acid, pyrosulphuric acid, perchloric acid, nitric acid, halogenosulphonic acids such as fluorosulphonic acid, chlorosulphonic acid or trifluoromethane sulphonic acid, methane sulphonic acid, ethane sulphonic acid, ethane disulphonic acid, benzene sulphonic acid, benzene disulphonic acids, toluene sulphonic acids, naphthalene sulphonic acids and naphthalene disulphonic acids.

Of these acids, use is preferably made of perchloric acid, trifluoromethane sulphonic acid, paratoluene sulphonic acid, chlorosulphonic acid, fluorosulphonic acid, methane-sulphonic acid.

Most particularly, perchloric acid or trifluoromethane sulphonic acid is selected.

The amount of acid expressed in relation to the number of proton equavalents to the number of moles of hydrogen peroxide can vary between about $1.10^{-4}$ and about 1.0.

One preferred variant of the process of the invention consists in selecting a $H^+/H_2O_2$ ratio of between $1.10^{-3}$ and 0.1.

One preferred variant of the process of the invention consists in adding a complexing agent for the metallic ions present in the medium since these latter have a detrimental effect on efficiency of the process of the invention, particularly in the case of phenols where yields of hydroxylation products are low. Consequently, it is preferable to inhibit the action of the metallic ions.

The metallic ions which are harmful to the efficiency of the hydroxylation process are transition metal ions and more particularly iron, copper, chromium, cobalt, manganese and vanadium ions.

The metallic ions are brought by the reagents, in particular the aromatic compounds and apparatus used. To inhibit the action of these metallic ions, it is sufficient to carry out the reaction in the presence of one or more complexing agents which is/are stable in relation to hydrogen peroxide, and which give complexes which are not able to be decomposed by the strong acids present and wherein the metal is no longer able to exercise a chemical activity.

Non-limitative examples of complexing agents can be cited, in particular, as various phosphoric acids, for example, such as orthophosphoric acid, metaphosphoric acid, pyrophosphoric acid, polyphosphoric acids, phosphonic acids such as (1-hydroxy ethylidene) diphosphonic acid, phosphonic acid, ethylphosphonic acid, phenylphosphonic acid.

It is also possible to use the afore-mentioned acid esters, and more particular mention can be made of the mono- or dialkyl orthophosphates, mono- or dicycloalkyl orthophosphates, mono- or dialkylaryl orthophosphates, for example, ethyl phosphate or diethyl phosphate, hexyl phosphate, cyclo hexyl phosphate, benzyl phosphate.

The amount of complexing agent depends on the metallic ion content of the reaction medium.

The amount of complexing agent expressed in numbers of moles of complexing agent per mole of hydrogen peroxide varies advantageously between 0.0001 and 0.01.

Another embodiment of the process of the invention consists in carrying out the process for monohydroxylation of phenolic compounds of general formula (I) using hydrogen peroxide in the presence of an effective amount of an alkaline metal salt or alkaline-earth metal salt of a strong acid, in the presence of an effective amount of at least one phosphorus oxacid, an effective amount of at least one ketonic compound corresponding to the general formula (II), said process being characterised by the fact that the reaction is carried out in the presence of a polar aprotic solvent as defined hereinabove.

The term, "strong acid" is used to refer to an acid which has a pka in water of less than $-0.1$, preferably less than $-1.0$.

Of the acid salts satisfying this definition, it is preferable to use alkali metal salts or alkaline-earth metal salts of acids which are stable relative to oxydation by means of hydrogen peroxide.

Thus, the afore-mentioned alkali metal salts or alkaline-earth metal salts of strong acids are perfectly suitable.

The term, "alkaline metal" is used to refer in this text to the neutral salts of acids defined hereinabove of lithium, sodium, potassium, rubidium and cesium.

It is most frequently preferable to use sodium or potassium salts, and is still more preferable to use sodium salts for economical reasons.

Of these various salts, those most preferable can be cited as disodium sulphate, sodium perchlorate, sodium trifluoromethanesulphonate, sodium paratoluenesulphonate, sodium chlorosulphonate, sodium fluorosulphonate, sodium methanesulphonate.

The term, "alkaline-earth metal salts" is used in this text to refer to neutral salts of the acids, defined hereinabove, of beryllium, magnesium, calcium, strontium and barium.

Preferably, magnesium, calcium and barium salts are most frequently used.

Of these various alkaline-earth metal salts, use is made preferably of calcium sulphate, magnesium sulphate, calcium perchlorate, magnesium perchlorate, calcium trifluoromethanesulphonate, magnesium trifluoromethanesulphonate, calcium paratoluenesulphonate, magnesium paratoluenesulphonate, calcium paratoluenesulphonate, magnesium paratoluenesulphonate, calcium fluorosulphonate, magnesium fluorosulphonate, calcium methanesulphonate, magnesium methanesulphonate.

It is possible to use mixtures of several alkali or alkaline-earth metal salts.

It is also possible to prepare the alkali metal salts or alkaline-earth metal salts in situ, for example by loading stoichiometric quantities of acid and oxide or hydroxide of these metals.

The phosphorus oxacids are more particularly compounds of an acid function containing phosphorus having an oxidation degree of 5.

It is also possible to use compounds of an acid function containing phosphorus having an oxidation degree of 3, which are oxidised in the medium by the hydrogen peroxide into corresponding compounds of phosphorus V; however, this is of no special interest, and it also has the drawback of consuming some of the hydrogen peroxide.

Of these oxacids of phosphorus V, it is possible to cite by way of example orthophosphoric acid, metaphosphoric acid, pyrophosphoric acid. polyphosphoric acids, phosphonic acids such as (1-hydroxyethylidene) diphosphonic acid, phosphonic acid, ethylphosphonic acid, phenyl phosphonic acid.

Those most frequently used because they are practical and economical are orthophosphoric acid, pyrophosphoric acid and (1-hydroxyethylidene) diphosphonic acid.

The amount of alkali metal salt or alkaline-earth metal salt used in the process of the invention can vary greatly.

Usually, this amount is expressed as a molar ratio of alkali metal salt or alkaline-earth metal salt/hydrogen peroxide. This ratio is most frequently between 0.001 and 0.10, and preferably between 0.005 and 0.05.

The amount of phosphorus oxacid expressed in a molar ratio of phosphorus oxacid/hydrogen peroxide is most Frequently between 0.001 and 0.20, preferably between 0.05 and 0.10.

As far as the conditions of implementation of the hydrogen peroxide and ketonic compound corresponding to formula (II) are concerned, these latter are the same as described hereinabove.

In accordance with the process of the invention, hydroxylation of the phenolic compound of formula (I) is carried out at a temperature which can be between 45° C. and 150° C.

One preferred variant of the process of the invention consists in selecting a temperature of between 45° C. and 75° C.

The reaction is advantageously carried out at atmospheric pressure.

From a practical point of view the process according to the invention is simple to use in continuous or discontinuous mode.

Preferably, the Following order of reagents is selected: the phenolic compound of formula (I), the polar aprotic organic solvent, possibly the complexing agent, the strong acid and then the ketonic compound of formula (II) are introduced.

The reaction medium is brought to the desired temperature and then the solution of hydrogen peroxide is added gradually.

At the end of the reaction, the non-transformed phenolic compound and the ketonic compound of formula (II) are separated from the hydroxylation products using conventional means, in particular by distillation, and are conveyed back to the reaction zone.

Some examples of the invention will now be given.

The following examples illustrate the invention without being limitative.

Examples 1 to 21 illustrate us of a polar aprotic organic solvent of low basicity.

Examples 22 to 35 are examples of the use of an aprotic organic solvent of low polarity and basicity.

The tests a to p are comparative examples.

In the examples, the following abbreviations mean:

$$TT = \frac{\text{number of moles of hydrogen peroxide transformed}}{\text{number of moles of hydrogen peroxide introduced}} \%$$

$$RT_{HQ} = \frac{\text{number of moles of hydroquinone formed}}{\text{number of moles of hydrogen peroxide transformed}} \%$$

$$RT_{PC} = \frac{\text{number of moles of pyrocatechol formed}}{\text{number of moles of hydrogen peroxide transformed}} \%$$

EXAMPLES

The following mode of operation will apply in all the examples.

47 g (0.50 mol ) phenol, x g of a ketonic compound of formula (II) are introduced into a round-bottomed glass flask of capacity 100 ml provided with a central agitation means, a condenser, a casting funnel and a thermometer.

y g of aprotic solvent and z g of strong acid (perchloric acid or sulphuric acid) is then introduced.

The various amounts (x, y and z) can be determined on the basis of the data in the recapitulating tables.

The reaction mixture is brought to the selected reaction temperature of 75° C. (unless stated otherwise), whilst keeping it under agitation conditions at 1200 revs/min.

A casting funnel is used to introduce an amount of aqueous solution with 70.5% by weight of hydrogen peroxide, over a period of 2 minutes, as specified in the following tables.

The reaction mixture is kept under agitation conditions at 75° C. for the period of time mentioned in the following tables.

The reaction mixture is then cooled, and the reaction products are applied in measured doses: the residual hydrogen peroxide is measured by iodometry and the diphenols formed are dosed by high performance, liquid chromatography.

Examples 1 to 4

Comparative tests a to e

In this series of examples, two solvents are used which are selected in accordance with the invention, namely:

sulpholane (tetramethylene sulphone): examples 1 and 2, propylene carbonate: examples 3 and 4.

The tests are carried out in accordance with the mode of operation given hereinabove.

All the conditions and results obtained are grouped in Table (I) overleaf:

TABLE I

HYDROXYLATION OF PHENOL USING $H_2O_2$/$HClO_4$/KETONIC COMPOUND OF FORMULA (II)

| Ref. | Ketonic compound (II) [ketonic compound (II)/ $H_2O_2$ molar ratio] | Organic Solvent [organic solvent/ phenol molar ratio] | $H_2O_2$/PHENOL molar ratio | $HClO_4$/$H_2O_2$ molar ratio | Duration | TT | $RT_{HQ}$ | $RT_{PC}$ | HQ/PC ratio |
|---|---|---|---|---|---|---|---|---|---|
| 1 | benzophenone (0.97) | sulpholane (0.249) | $5.2 \times 10^{-2}$ | $1.2 \times 10^{-2}$ | 37 mins | 92 | 46.5 | 40.5 | 1.15 |
| 2 | benzophenone (0.985) | sulpholane (0.498) | $5.05 \times 10^{-2}$ | $1.25 \times 10^{-2}$ | 60 mins | 100 | 49.0 | 37.5 | 1.31 |
| 3 | benzophenone (0.98) | propylene carbonate (0.25) | $5.1 \times 10^{-2}$ | $1.25 \times 10^{-2}$ | 35 mins | 100 | 45.5 | 41.0 | 1.11 |
| 4 | benzophenone (0.99) | propylene carbonate (0.495) | $5.0 \times 10^{-2}$ | $1.35 \times 10^{-2}$ | 45 mins | 98.5 | 45 | 37.5 | 1.20 |
| a | benzophenone (1.0) | without | $4.9 \times 10^{-2}$ | $1.35 \times 10^{-2}$ | 3 mins | 100 | 43 | 42 | 1.02 |
| b | without | sulpholane (0.245) | $5.0 \times 10^{-2}$ | $1.25 \times 10^{-2}$ | 150 mins | 98 | 34.5 | 45 | 0.77 |
| c | without | propylene carbonate (0.245) | $5.2 \times 10^{-2}$ | $1.25 \times 10^{-2}$ | 60 mins | 98 | 38 | 49.5 | 0.77 |
| d | benzophenone (1.0) | dimethylformamide (0.25) | $5.0 \times 10^{-2}$ | $1.50 \times 10^{-2}$ | 120 mins | 21.5 | 16 | 33.5 | 0.48 |
| e | benzophenone (0.98) | hexamethylenephosphoramide (0.115) | $5.1 \times 10^{-2}$ | $1.25 \times 10^{-2}$ | 120 mins | 9.0 | 0.5 | 3.5 | 0.14 |
| f | benzophenone (0.98) | methanol (0.24) | $5.1 \times 10^{-2}$ | $1.25 \times 10^{-2}$ | 85 mins | 100 | 37 | 39 | 0.95 |

As a comparison, the results obtained when carrying out the process of the invention are given:

test a: in the absence of an organic solvent,
test b and c: in the absence of benzophenone but in the presence of an organic solvent, sulpholane and propylene carbonate respectively,
test d and e: in the presence of an organic solvent with a strong dielectric constant such as dimethylformamide (test d) and hexamethylene phosphoramide (test e),
test f: in the presence of benzophenone and in the presence of a protic solvent such as methanol.

By studying Table I it is clear that the presence of a polar organic solvent such as that defined according to the invention promotes the formation of hydroquinone.

Examples 5 to 12

Comparative test g

In this series of examples, the following solvents are used which are selected in accordance with the invention, namely:

acetonitrile: examples 5 to 8,
butyronitrile: example 9,
benzonitrile: example 10,
nitromethane: example 11,
nitrobenzene: example 12.

The tests are carried out using the mode of operation defined hereinabove.

All the conditions and results obtained are shown in Table (II) overleaf:

TABLE II

HYDROXYLATION OF PHENOL USING $H_2O_2$/$HClO_4$/KETONIC COMPOUND OF FORMULA (II)

| Ref. | Ketonic compound (II) [ketonic compound (II)/ $H_2O_2$ molar ratio] | Organic Solvent [organic solvent/ phenol molar ratio] | $H_2O_2$/PHENOL molar ratio | $HClO_4$/$H_2O_2$ molar ratio | Duration | TT | $RT_{HQ}$ | $RT_{PC}$ | HQ/PC ratio |
|---|---|---|---|---|---|---|---|---|---|
| 5 | benzophenone (0.96) | acetonitrile (0.25) | $5.20 \times 10^{-2}$ | $1.5 \times 10^{-2}$ | 35 mins | 100 | 44.5 | 40.5 | 1.10 |
| 6 | benzophenone (1.0) | acetonitrile (0.50) | $5.0 \times 10^{-2}$ | $1.45 \times 10^{-2}$ | 40 mins | 100 | 47 | 37.5 | 1.25 |
| 7 | benzophenone (0.49) | acetonitrile (0.75) | $5.10 \times 10^{-2}$ | $0.65 \times 10^{-2}$ | 250 mins | 97.5 | 47.5 | 39.5 | 1.20 |
| 8 | benzophenone (1.0) | acetonitrile (1.00) | $5.15 \times 10^{-2}$ | $1.25 \times 10^{-2}$ | 120 mins | 98 | 48.5 | 36.5 | 1.33 |
| 9 | benzophenone (0.98) | butyronitrile (0.25) | $5.05 \times 10^{-2}$ | $1.15 \times 10^{-2}$ | 60 mins | 100 | 45.5 | 40.5 | 1.12 |
| 10 | benzophenone (0.98) | benzonitrile (0.23) | $4.70 \times 10^{-2}$ | $1.10 \times 10^{-2}$ | 60 mins | 100 | 45.5 | 40.5 | 1.12 |
| 11 | benzophenone (1.0) | nitrobenzene (0.24) | $4.8 \times 10^{-2}$ | $1.30 \times 10^{-2}$ | 15 mins | 100 | 41.5 | 38.0 | 1.09 |
| 12 | benzophenone (0.98) | nitrobenzene (0.25) | $5.2 \times 10^{-2}$ | $1.35 \times 10^{-2}$ | 30 mins | 100 | 43.5 | 39.0 | 1.12 |
| a | benzophenone (1.0) | without | $4.9 \times 10^{-2}$ | $1.35 \times 10^{-2}$ | 3 mins | 100 | 43 | 42 | 1.02 |
| g | without | acetonitrile (0.25) | $5.0 \times 10^{-2}$ | $1.30 \times 10^{-2}$ | 120 mins | 98 | 38 | 44.5 | 0.85 |

As a comparison, the results obtained are given when the process of the invention is carried out:

test a: in the absence of an organic solvent,
test g: in the absence of benzophenone but in the presence of an organic solvent acetonitrile.

It emerges from looking at Table (II) that the presence of a polar organic solvent such as defined according to the invention promotes the formation of hydroquinone.

Examples 13 and 14

In these examples, the mode of operation is the same as hereinabove, except that the reaction temperature is 45° C. in Example 13 and 100° C. in Example 14.

All the conditions and results obtained are grouped in Table (III) overleaf.

TABLE III

HYDROXYLATION OF PHENOL USING $H_2O_2/HClO_4$/KETONIC COMPOUND OF FORMULA (II)

| Ref. | Ketonic compound (II) [ketonic compound (II)/ $H_2O_2$ molar ratio] | Organic Solvent [organic solvent/ phenol molar ratio] | $H_2O_2$/PHENOL molar ratio | $HClO_4/H_2O_2$ molar ratio | Temperature °C. | Duration | TT | $RT_{HQ}$ | $RT_{PC}$ | HQ/PC ratio |
|---|---|---|---|---|---|---|---|---|---|---|
| 13 | benzophenone (0.985) | sulpholane (0.25) | $5.05 \times 10^{-2}$ | $1.25 \times 10^{-2}$ | 45° C. | 2 h 30 | 98 | 49.5 | 36.0 | 1.38 |
| 14 | benzophenone (0.955) | sulpholane (0.25) | $5.2 \times 10^{-2}$ | $1.1 \times 10^{-2}$ | 100° C. | 10 mins | 99.5 | 44.5 | 37.5 | 1.19 |

Examples 15 and 16

In these examples, the mode of operation is the same as that given hereinabove, except that perchloric acid is replaced by sulphuric acid.

All the conditions and results obtained are grouped in Table (IV) overleaf:

TABLE IV

HYDROXYLATION OF PHENOL USING $H_2O_2/H_2SO_4$/KETONIC COMPOUND OF FORMULA (II)

| Ref. | Ketonic compound [ketonic compound (II)/ $H_2O_2$ molar ratio] | Organic Solvent [organic solvent/ phenol molar ratio] | $H_2O_2$/PHENOL molar ratio | $H_2SO_4/H_2O_2$ molar ratio | Duration | TT | $RT_{HQ}$ | $RT_{PC}$ | HQ/PC ratio |
|---|---|---|---|---|---|---|---|---|---|
| 15 | benzophenone (1.0) | acetonitrile (0.25) | $5.0 \times 10^{-2}$ | $1.3 \times 10^{-2}$ | 60 mins | 100 | 48 | 42 | 1.14 |
| 16 | benzophenone (0.99) | sulpholane (0.485) | $4.9 \times 10^{-2}$ | $1.55 \times 10^{-2}$ | 60 mins | 98.5 | 46.5 | 39 | 1.19 |

Examples 17 and 18

In the following two examples, a ketonic compound is used which is different from the preceding examples.

The ketonic compound is in the form of benzophenones substituted by an electron donor group:

4,4'-dimethoxybenzophenone: Example 17,
4,4'-dimethyl benzophenone: Example 18.

All the conditions and results obtained are grouped together in Table (V) overleaf:

TABLE V

HYDROXYLATION OF PHENOL USING $H_2O_2/HClO_4$/KETONIC COMPOUND OF FORMULA (II)

| Ref. | Ketonic compound (II) [ketonic compound (II)/ $H_2O_2$ molar ratio] | Organic Solvent [organic solvent/ phenol molar ratio] | $H_2O_2$/PHENOL molar ratio | $HClO_4/H_2O_2$ molar ratio | Duration | TT | $RT_{HQ}$ | $RT_{PC}$ | HQ/PC ratio |
|---|---|---|---|---|---|---|---|---|---|
| 17 | 4,4'-dimethoxy benzophenone (0.925) | acetonitrile (0.255) | $5.4 \times 10^{-2}$ | $1.4 \times 10^{-2}$ | 1 h 45 | 99.5 | 45 | 37.5 | 1.2 |
| 18 | 4,4'-dimethyl benzophenone (1.0) | acetonitrile (0.25) | $4.95 \times 10^{-2}$ | $1.7 \times 10^{-2}$ | 32 mins | 100 | 51 | 39.5 | 1.29 |

It is noted that good reaction yields are obtained and that high hydroquinone/pyrocatechol ratios are obtained.

Examples 19 to 21

Comparative tests h and i

In the following two examples, a ketonic compound is used which is different from in the previous examples.

The ketonic compound is in the form of the following ketonic compounds corresponding to the formula (II):

2-pentanone: Example 19,
acetophenone: Examples 20 and 21.

As a comparison, the results of tests without any organic solvent are given.

All the conditions and results obtained are grouped together in Table (VI) overleaf:

TABLE VI

HYDROXYLATION OF PHENOL USING $H_2O_2/HClO_4$/KETONIC COMPOUND OF FORMULA (II)

| Ref. | Ketonic compound (II) [ketonic compound (II)/ $H_2O_2$ molar ratio] | Organic Solvent [organic solvent/ phenol molar ratio] | $H_2O_2$/PHENOL molar ratio | $HClO_4/H_2O_2$ molar ratio | Duration | TT | $RT_{HQ}$ | $RT_{PC}$ | HQ/PC ratio |
|---|---|---|---|---|---|---|---|---|---|
| 19 | 2-pentanone (1.0) | acetonitrile (0.50) | $5.1 \times 10^{-2}$ | $1.15 \times 10^{-2}$ | 5 mins | 100 | 41.5 | 44.5 | 0.93 |
| 20 | acetophenone (1.0) | acetonitrile (0.25) | $5.0 \times 10^{-2}$ | $1.25 \times 10^{-2}$ | 10 mins | 100 | 37 | 48 | 0.77 |
| 21 | acetophenone (0.96) | sulpholane (0.25) | $5.15 \times 10^{-2}$ | $1.35 \times 10^{-2}$ | 15 mins | 100 | 38.5 | 47 | 0.82 |
| h | 2-pentanone (1.0) | without | $5.1 \times 10^{-2}$ | $1.35 \times 10^{-2}$ | 3 mins | 100 | 36 | 50.5 | 0.71 |
| i | acetophenone (1.0) | without | $5.1 \times 10^{-2}$ | $1.25 \times 10^{-2}$ | 2 mins | 100 | 34.5 | 49 | 0.70 |

By comparing Examples 19, 20, 21 and the comparative tests h and i, it is clear that by adding an organic solvent it is possible to increase the amount of hydroquinone Formed, irrespective of the type of ketone used.

Examples 22 to 31

Comparative Tests j to m

In this series of examples, various solvents are used which are selected in accordance with the invention, namely:

di n-propyl oxide: Example 22,
methyl t-butyl ether: Examples 23 and 24,
1,2-dimethoxy ethane: Example 25,
tetrahydrofuran: Examples 26 and 27,
dioxane: Examples 28 and 29,
triethyl phosphate: Example 30,
tributyl phosphate: Example 31.

The examples are carried out according to the mode of operation defined hereinabove.

All the conditions and results obtained are grouped together in Table (V) overleaf:

test j: in the absence of an organic solvent,
test k and l in the presence of benzophenone and in the presence of an organic solvent with a strong dielectric constant such as dimethylformamide (test k) and hexamethylenephosphoramide (test l),
test m: in the presence of benzophenone and a protic solvent such as methanol.

By studying Table (V) it can clearly be seen that the presence of an organic solvent such as defined according to the invention promotes the formation of hydroquinone.

Examples 32 and 33

Comparative Tests n and o

A series of tests is carried out using diisopropyl oxide as the organic solvent.

All the operating conditions and results are shown in Table (VI) overleaf:

As a comparison, two tests have also been carried out without organic solvent.

It is noted that the presence of organic solvent per-

TABLE V

| | HYDROXYLATION OF PHENOL USING $H_2O_2$/$HClO_4$/KETONIC COMPOUND OF FORMULA (II) | | | | | | | | |
|---|---|---|---|---|---|---|---|---|---|
| Ref. | Ketonic compound (II) [ketonic compound (II)/ $H_2O_2$ molar ratio] | Organic Solvent [organic solvent/ phenol molar ratio] | $H_2O_2$/PHENOL molar ratio | $HClO_4$/$H_2O_2$ molar ratio | Duration | TT | $RT_{HQ}$ | $RT_{PC}$ | HQ/PC ratio |
| 22 | benzophenone (0.97) | di n-propyl oxide (0.25) | $5.25 \times 10^{-2}$ | $1.1 \times 10^{-2}$ | 100 mins | 99.5 | 45 | 42 | 1.07 |
| 23 | benzophenone (0.91) | methyl t-butyl ether (0.025) | $5.5 \times 10^{-2}$ | $1.3 \times 10^{-2}$ | 40 mins | 100 | 45 | 42 | 1.07 |
| 24 | benzophenone (1.0) | methyl t-butyl ether (0.062) | $5.0 \times 10^{-2}$ | $1.2 \times 10^{-2}$ | 60 mins | 100 | 40 | 35.5 | 1.13 |
| 25 | benzophenone (0.99) | 1,2-dimethoxy ethane (0.12) | $5.0 \times 10^{-2}$ | $1.15 \times 10^{-2}$ | 45 mins | 99.5 | 46 | 42.5 | 1.08 |
| 26 | benzophenone (0.97) | tetrahydrofuran (0.12) | $4.95 \times 10^{-2}$ | $1.15 \times 10^{-2}$ | 90 mins | 100 | 41 | 38.5 | 1.06 |
| 27 | benzophenone (0.96) | tetrahydrofuran (0.25) | $5.2 \times 10^{-2}$ | $1.15 \times 10^{-2}$ | 110 mins | 100 | 44.5 | 40.5 | 1.10 |
| 28 | benzophenone (0.97) | dioxane (0.12) | $4.9 \times 10^{-2}$ | $1.3 \times 10^{-2}$ | 60 mins | 100 | 45 | 42.5 | 1.06 |
| 29 | benzophenone (0.95) | dioxane (0.25) | $5.3 \times 10^{-2}$ | $1.25 \times 10^{-2}$ | 120 mins | 100 | 48 | 41.0 | 1.17 |
| 30 | benzophenone (1.0) | triethyl phosphate ((0.083) | $5.25 \times 10^{-2}$ | $1.40 \times 10^{-2}$ | 60 mins | 100 | 42.5 | 37.5 | 1.13 |
| 31 | benzophenone (1.0) | tributyl phosphate (0.025) | $5.0 \times 10^{-2}$ | $1.15 \times 10^{-2}$ | 60 mins | 100 | 45 | 41.5 | 1.08 |
| j | benzophenone (1.0) | without | $4.9 \times 10^{-2}$ | $1.35 \times 10^{-2}$ | 3 mins | 100 | 43 | 42 | 1.02 |
| k | benzophenone (1.0) | dimethylformamide (0.25) | $5.0 \times 10^{-2}$ | $1.50 \times 10^{-2}$ | 120 mins | 21.5 | 16 | 33.5 | 0.48 |
| l | benzophenone (0.98) | hexamethylenephosphoramide (0.115) | $5.1 \times 10^{-2}$ | $1.25 \times 10^{-2}$ | 120 mins | 9.0 | 0.5 | 3.5 | 0.14 |
| m | benzophenone (0.98) | methanol (0.24) | $5.1 \times 10^{-2}$ | $1.25 \times 10^{-2}$ | 85 mins | 100 | 37 | 39 | 0.95 |

As a comparison, the results are given which were obtained when the process of the invention was carried out:

mits an increase in the amount of hydroquinone formed.

TABLE VI

| | HYDROXYLATION OF PHENOL USING $H_2O_2$/$HClO_4$/KETONIC COMPOUND OF FORMULA (II) | | | | | | | | |
|---|---|---|---|---|---|---|---|---|---|
| Ref. | Ketonic compound (II) [ketonic compound (II)/ $H_2O_2$ molar ratio] | Organic Solvent [organic solvent/ phenol molar ratio] | $H_2O_2$/PHENOL molar ratio | $HClO_4$/$H_2O_2$ molar ratio | Duration | TT | $RT_{HQ}$ | $RT_{PC}$ | HQ/PC ratio |
| 32 | benzophenone (0.975) | diisopropyl oxide (0.125) | $5.1 \times 10^{-2}$ | $0.6 \times 10^{-2}$ | 120 mins | 100 | 45.5 | 41.5 | 1.10 |
| 33 | benzophenone (1.0) | diisopropyl oxide (0.25) | $5.0 \times 10^{-2}$ | $1.35 \times 10^{-2}$ | 90 mins | 98 | 44.0 | 40.5 | 1.09 |
| n | without | diisopropyl oxide (0.125) | $5.0 \times 10^{-2}$ | $1.45 \times 10^{-2}$ | 230 mins | 99.5 | 38 | 43 | 0.88 |
| o | without | diisopropyl oxide (0.50) | $5.0 \times 10^{-2}$ | $1.45 \times 10^{-2}$ | 375 mins | 96 | 34 | 36.5 | 0.93 |

Examples 34 and 35

Comparative test p

In the following two examples, a different ketonic compound was used from in the preceding examples.

The ketonic compound used was acetophenone.

As a comparison, the results of tests have given which were carried out in the absence of an organic solvent (test p).

All the conditions and results obtained are grouped together in Table (VII) overleaf:

TABLE VII

HYDROXYLATION OF PHENOL USING $H_2O_2/HClO_4$/KETONIC COMPOUND OF FORMULA (II)

| Ref. | Ketonic compound (II) [ketonic compound (II)/ $H_2O_2$ molar ratio] | Organic Solvent [organic solvent/ phenol molar ratio] | $H_2O_2$/PHENOL molar ratio | $HClO_4/H_2O_2$ molar ratio | Duration | TT | $RT_{HQ}$ | $RT_{PC}$ | HQ/PC ratio |
|---|---|---|---|---|---|---|---|---|---|
| 34 | acetophenone (0.93) | diisopropyl oxide (0.12) | $5.25 \times 10^{-2}$ | $1.15 \times 10^{-2}$ | 16 mins | 100 | 37 | 49 | 0.76 |
| 35 | acetophenone (1.0) | diisopropyl oxide (0.25) | $5.1 \times 10^{-2}$ | $1.20 \times 10^{-2}$ | 90 mins | 100 | 40.5 | 47 | 0.86 |
| p | acetophenone (0.975) | without | $5.1 \times 10^{-2}$ | $1.25 \times 10^{-2}$ | 2 mins | 100 | 34.5 | 49 | 0.70 |

On studying Table (VII) it is clear that the presence of an organic solvent such as defined according to the invention promotes the formation of hydroquinone.

We claim:

1. A process for the hydroxylation of an aromatic compound having both an —OR group and a hydrogen atom attached to the aromatic ring with the hydrogen atom being in the para position to the —OR group, where R is a hydrogen atom or a hydrocarbon radical having 1 to 24 carbon atoms which can be saturated or unsaturated, linear or branched aliphatic radicals or a saturated or unsaturated, or aromatic, monocyclic, bicyclic, or polycyclic cycloaliphatic radical, comprising reacting the aromatic compound with hydrogen peroxide in the presence of effective amounts of a strong acid, a ketonic compound, and a polar aprotic organic solvent having a basicity donor number less than 25.

2. A process according to claim 1, wherein the organic solvent is a polar organic solvent with a dielectric constant not less than 20.

3. A process according to claim 2 wherein the polar solvent organic solvent has a donor number less than or equal to 20.

4. A process according to claim 2 wherein the polar organic solvent is selected from nitrated compounds, aliphatic or aromatic nitriles, tetramethylene sulphone, and propylene carbonate.

5. A process according to claim 2 wherein the polar organic solvent is selected from the following solvents: nitromethane, nitroethane, 1-nitropropane, 2-nitropropane or mixtures thereof, nitrobenzene, acetonitrile, propionitrile, butanenitrile, isobutanenitrile, benzonitrile, benzyl cyanide, tetramethylene sulfphone (sulpholane), and propylene carbonate.

6. A process according to claim 1 wherein the organic solvent is a polar organic solvent with a dielectric constant of less than about 20.

7. A process according to claim 6 wherein the polar organic solvent has a donor number not less than 15.

8. A process according to claim 6 wherein the polar organic solvent is selected from among aliphatic, cycloaliphatic or aromatic ether-oxides, phosphoric neutral esters, and ethylene carbonate.

9. A process according to claim 6 wherein the polar organic solvent is selected from the following solvents: diethyl oxide, dipropyl oxide, diisopropyl oxide, dibutyl oxide, methyl t-butyl ether, dipentyl oxide, diisopentyl oxide, ethleneglycol dimethylether (or 1,2-dimethoxyethane), diethyl glycol dimethylether (or 1,5-dimethoxy-3-oxapentane), dioxane, tetrahydrofuran, trimethyl phosphate, triethyl phosphate, butyl phosphate, triisobutyl phosphate, tripentyl phosphate, and ethylene carbonate.

10. A process according to claim 1 wherein the ketonic compound corresponds to the formula (II):

$$R_a\text{—CO—X—}R_b \qquad (II)$$

in which:

$R_a$ and $R_b$ which may be the same or different, represent hydrocarbon radicals having 1 to 30 carbon atoms, or together form a divalent radical which may be substituted by at least one halogen atom or functional group which is stable under reaction conditions, X represents a valency linkage, a —CO— group, a —CHOH group, or a —(R)$_n$— group, R representing an alkylene group having 1 to 4 carbon atoms and n is a whole number between 1 and 16.

11. A process according to claim 10 wherein $R_a$ and $R_b$ represent:

linear or branched alkyl radicals, linear or branched alkenyl radicals, cycloalkyl or cycloalkenyl radicals with 4 to 6 carbon atoms, mono-, bi-, or polycyclic aryl radicals wherein the cycles between them either form an ortho system or an ortho and pericondensed systems, or aryl alkyl or aryl alkenyl radicals, with the proviso that $R_a$ and $R_b$ can together form an alkylene group.

12. A process according to claim 1 wherein the ketonic compound corresponds to formula (IIa):

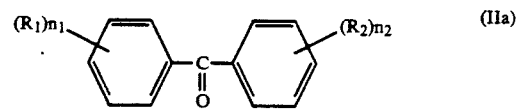

in which formula (IIa):

$R_1$ and $R_2$ which may be the same or different represent a hydrogen atom or an electron-donor group, $n_1$, $n_2$, which may be the same or different, is the two carbon atoms disclosed in the aposition to the two carbon atoms bearing the —CO group can be linked together by a valency linkage or by a —$CH_2$— group to form a cycloketone which may be saturated or unsaturated.

13. A process according to claim 12 wherein the ketonic compound is selected from: acetone, 3,3-dimethyl-2-butanone, methylvinylketone, mesityl oxide, 2,4-dimethyl-3-pentanone, diacetyl, dicyclohexylketone, acetophenone, benzophenone, 2-methylbenzophenone, 2,4-dimethylbenzophenone, 4,4'-dimethoxybenzophenone, 2,2'-dimethylbenzophenone, 4,4'-dimethoxybenzonphenone, 4-hydroxybenzophenone, 4,4-dihydroxybenzophenone, 4-benzoylbiphenyl, benzoin, 4,4'-dihydroxybenzoin, 2,4-dimethylbenzoin, 4,4'-dimethylbenzoin, 4,4-dimethoxybenzoin, 4,4'-difluorobenzoin, α-methoxybenzoin, β-ethoxybenzoin, deoxybenzoin, 4-hydroxydeoxybenzoin, 4-methyl-deoxybenzoin, 4-methoxy-deoxybenzoin, 4,4-dimethoxy-deoxybenzoin, 4,4'-difluoro-deoxybenzoin, benzalacetone, benzile, cyclohexanone, α-isophorone, cyclohexenylcyclohexanone, or fluorenone.

14. A process according to claim 1 wherein the ketonic compound is a para-selective ketone.

15. A process according to one of claims 2 to 14 and 1, wherein the aromatic compound corresponds to the formula (I):

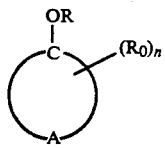

wherein:
- A is a residue of a monocyclic, bicyclic, or polycyclic aromatic carbocyclic radical or a divalent radical constituted of a chain of two or more monocyclic aromatic carbocyclic radicals,
- R represents a hydrogen atom or a hydrocarbon radical with 1 to 24 carbon atoms which can be a saturated or unsaturated, linear or branched aliphatic radical, or a saturated or unsaturated, or aromatic, monocyclic or polycyclic cycloaliphatic radical,
- $R_o$ represents at least one substituent which may be the same or different,
- n is 1-4.

16. A process according to claim 15, wherein the radical R is
- a hydrogen atom,
- a linear or branched alkyl radical with 1 to 6 carbon atoms,
- a cyclohexyl radical,
- a phenyl radical, or
- a benzyl radical, and
the $R_o$ radical(s) is
- a hydrogen atom
- a linear or branched alkyl radical with 1 to 6 carbon atoms,
- a linear or branched alkenyl radical with 2 to 6 carbon atoms,
- an alkoxy radical of the $R_1$—O— type wherein $R_1$ represents a linear or branched alkyl radical with 1 to 6 carbon atoms,
- an alkyl group with 2 to 6 carbon atoms,
- a —$COOR_2$-group, where $R_2$ represents a linear or branched alkyl radical with 1 to 4 carbon atoms,
- a halogen atom, or
- a —$CF_3$ group.

17. A process according to claim 16 wherein n is 0, 1, 2 or 3.

18. A process according to claim 15 wherein:

- $R_o$ represents a hydrogen atom, a linear or branched alkyl or alkoxy radical with 1 to 6 carbon atoms, a cyclohexyl radical, a phenyl radical,
- B symbolises a valency linkage, an alkylene or alkylidene radical with 1 to 4 carbon atoms or an oxygen atom,
- m is 0 or 1,
- n is 0, 1 or 2,
- p is 0 or 1.

19. A process according to one of claims 2-14 and 1 wherein the aromatic compound corresponds to the general formula (I'):

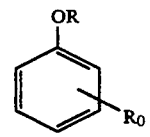

wherein R and $R_o$ which may be the same or different represent a hydrogen atom, an alkyl radical with 1 to 4 carbon atoms, a cyclohexyl radical, a phenyl radical.

20. A process according to claim 15 wherein the compound of formula (I) is selected from: phenol, anisol, orthocresol, metacresol, and 2-methoxy phenol.

21. A process according to claim 20 wherein the compound of formula (I) is phenol.

22. A process according to claim 2 wherein the amount of solvent used is such that the molar ratio between the number of moles of the organic solvent and the number of moles of the aromatic compound between 0.1 and 2.0.

23. A process according to claim 15 wherein the amount of solvent used is such that the molar ratio between the number of moles of the organic solvent and the number of moles of the compound of formula (I) is between 0.01 and 0.25.

24. A process according to claim 1 wherein the amount of ketonic compound of formula (I) is at least $1.10^{-3}$ moles per mole of hydrogen peroxide.

25. A process according to claim 1 wherein the strong acid is an acid with a pKa in water of less than $-0.1$.

26. A process according to claim 1 wherein the strong acid is perchloric acid or trifluoro-methane sulphonic acid.

27. A process according to claim 1 wherein the amount of strong acid is such that the ratio $H^+/H_2O_2$ is between $1.10^{-4}$ and 1.0.

28. A process according to claim 15 wherein the molar ratio $H_2O_2$/phenolic compound of formula (I) is between 0.01 and 0.3.

29. A process according to claim 1 wherein the process is carried out at a temperature of between 50° C. and 150° C.

30. A process according to claim 15 wherein A is:
a monocyclic, bicyclic, or polycyclic aromatic carbocyclic radical with cycles capable of forming between them an orthocondensed system corresponding to formula

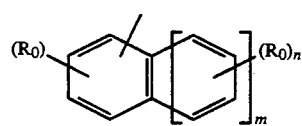

where m is 0, 1 or 2, or a radical constituted by a chain of two or more monocyclic aromatic carbocyclic radicals corresponding to the formula (Ib):

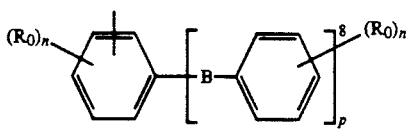

where p is 0, 1, 2 or 3 and B represents:
a valency linkage
an alkylene or alkylidene radical with 1 to 4 carbon atoms, or
one of the following groups:

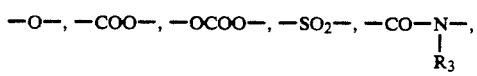

where $R_3$ represents a hydrogen atom, an alkyl radical with 1 to 4 carbon atoms, a cyclohexyl radical or a phenyl radical.

31. The process according to claim 2 wherein the solvent has a dielectric constant of between 25 and 75.

32. The process according to claim 2 wherein the solvent has a donor number of between 2 and 17.

33. The process according to claim 6 wherein the solvent has a dielectric constant of between 2 and 15.

34. The process according to claim 19 wherein R is a hydrogen atom and $R_o$ is a hydrogen atom, a methyl radical, or a methoxy radical.

35. The process according to claim 22 wherein the molar ratio is between 0.25 and 1.0.

36. The process according to claim 24 wherein the amount of ketonic compound is between 0.05 and 1.0 mol per mol of hydrogen peroxide.

37. The process according to claim 25 wherein the strong acid has a pKa in water of less than −0.

38. The process according to claim 28 wherein the molar ratio is between 0.05 and 0.10.

* * * * *